United States Patent [19]

Mori

[11] Patent Number: 4,676,226
[45] Date of Patent: Jun. 30, 1987

[54] LIGHT RAYS BATHTUB

[76] Inventor: Kei Mori, 3-16-3-501, Kaminoge, Setagaya-ku, Tokyo, Japan

[21] Appl. No.: 878,934

[22] Filed: Jun. 26, 1986

[30] Foreign Application Priority Data

Jul. 9, 1985 [JP] Japan .................................. 60-151152

[51] Int. Cl.⁴ ................................................ F24J 2/18
[52] U.S. Cl. ...................................... 126/439; 126/451
[58] Field of Search ............... 126/417, 438, 439, 440, 126/451; 350/96.10

[56] References Cited

U.S. PATENT DOCUMENTS 2,478,765  8/1949  Kim ...................................... 126/417
2,785,695  3/1957  Carey .................................... 126/451
3,023,753  3/1962  Wheless ............................... 126/451
4,201,197  5/1980  Dismer ................................. 126/451

Primary Examiner—James C. Yeung
Attorney, Agent, or Firm—Jordan and Hamburg

[57] ABSTRACT

A light rays bathtub has an inner surface formed as a reflection surface and an optical conductor for radiating visible light rays into the tub. The bathtub is so constructed that the visible light rays are radiated over the entire area in the tub. An entire body can bath effectively in the light rays consisting of only the visible light ray component not containing therein harmful ultraviolet, infrared or the like.

11 Claims, 2 Drawing Figures

4,676,226

LIGHT RAYS BATHTUB

BACKGROUND OF THE INVENTION

The present invention relates to a light rays bathtub, in particular, a light rays bathtub in which visible light rays are effectively applied to the entire surface of a human body's skin in order to promote a living body reaction on the surface of the skin and in the interior thereof.

In the recent years, the average life of a human has been fairly advanced day by day. And therefore, a large number of persons suffer from incurable diseases such as arthritis, neuralgia and rheumatism, or the pain of an injury or a bone fracture, or the pain of an ill-defined disease. Furthermore, any person cannot avoid having one's skin grow old which gradually progresses from a comparatively young age. On the other hand, the present applicant has previously proposed to focus solar rays or artifical light rays by use of lenses or the like, to guide the same into an optical conductor, and to transmit those rays onto an optional desired place through an optical conductor. The solar rays or artificial light rays transmitted in such a way are employed for use in illuminating or for other like purposes, for example, to cultivate plants, chlorella, or the like. In the process thereof, visible light rays not containing ultraviolet and infrared promote a living body reaction. For instance, those visible light rays have noticeable effects in stopping the pain of arthritis, neuralgia, rheumatism, injury, bone fracture, or the like. Such effects obtained by use of the device according to the present invention have been already found out by the present applicant.

In order to stop the pain of the various diseases as mentioned above, visible light rays of fairly strong intensity need to be concentratedly applied to the diseased part as a matter of course. However, even in the case of applying thereto weak light rays for a sufficiently long time, the same effect can be demonstrated depending on the condition of the illness. In practice, various medical treatments are performed by applying weak light rays to the diseased part, being limited to one particular part. And further, it is well known that sunbathing is useful for promoting a human body's health. However, ultaviolet or the like is contained in the solar rays and it exerts a bad influence on the skin of a human body. A person who is not so healthy from the first cannot bathe in the sun.

Furthermore, light rays such as ultraviolet, infrared or the like have an accumulation effect. Accumulating ultraviolet causes cancer, and accumulating infrared causes heat or is even in danger of producing a burn. Consequently, to the contrary, it is worse for health to bathe in light rays containing therein ultraviolet or infrared for a long time.

SUMMARY OF THE INVENTION

It is an object of the present invention to provide a light rays bathtub capable of bathing in light rays consisting of only the visible light ray component and not containing therein any harmful component such as ultraviolet, infrared or the like.

It is another object of the present invention to provide a light rays bathtub in which visible light rays radiated from an optical conductor are once reflected on the inner wall surface of the tub and thereafter pass through near the central portion of the tub.

It is another object of the present invention to provide a light rays bathtub in which a large number of radiation points for radiating visible light rays are provided almost uniformly on the entire inner wall surface of the tub.

The above-mentioned features and other advantages of the present invention will be apparent from the following detailed description which goes with the accompanying drawings.

DESCRIPTION OF THE PREFERRED EMBODIMENTS

Figure 1:
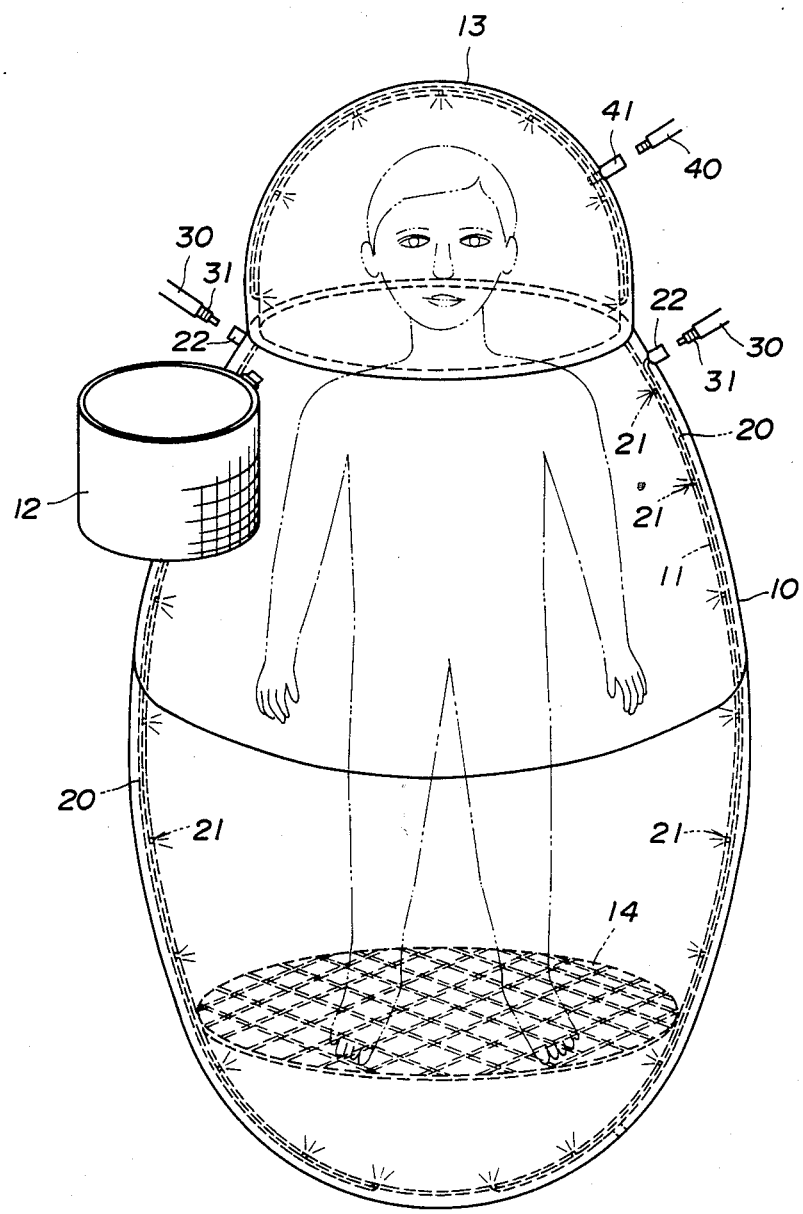
FIG. 1 is a perspective see-through view for explaining an embodiment of a light rays bathtub according to the present invention.

FIG. 1 is a perspective see-through view showing the interior for explaining an embodiment of a light rays bathtub according to the present invention. In FIG. 1, 10 is a light rays bathtub, the inner surface 11 of which is processed to form a mirror surface, and 20 is an optical conductor for supplying visible light rays into the light rays bathtub 10. The visible light rays radiated from the optical conductor 20 are reflected on the inner surface of the light rays bathtub 10 and radiated almost uniformly into the light rays bathtub 10. Moreover, radiation of the light rays into the light rays bathtub 10 is performed by the light rays radiating portion which is installed almost uniformly in the light rays bathtub 10 as shown in FIG. 1. On other occassions, strong light rays can be applied to a specified part, for instance, a shoulder portion of the human body. Or otherwise, the number of light rays radiation points is decreased a little more and the light rays emitted therefrom are directed to the inner wall surface of the light rays bathtub 10 and scatter about thereon.

As shown in FIG. 1, a naked person gets in the light rays bathtub 10 and bathes in the light rays radiated in such a manner as mentioned above. For this reason, the light rays bathtub 10 is so constructed as to be able to open and close in an optional desired manner that is well known. And further, since a person takes off one's clothes after getting in the bathtub 10, the same unitarily comprises an undressing basket 12 for putting one's clothes.

Furthermore, a top cover member 13 is constructed with transparent material so as to be able to see the outside after entering the light rays bathtub 10. The persn in the bathtub 10 is in communication with the outside and puts his or her clothes in the basket 12. Therefore, the top cover member 13 which is so constructed as to be able to open and close is closed. Moreover, in order to make contact with the outside, a wireless apparatus or a push-button switch for communication is provided in the light rays bathtub 10. It will be easily understood that such a well-known optional measure can be used for the purpose stated. And further, a transparent bottom plate 14 is placed on the lower portion of the light rays bathtub 10, and light rays are radiated from the underside of the bottom plate 14 so as to be able to supply light rays to the sole of a foot that usually doesn't receive the light rays at all. In such a manner, the supplied light rays serve for promoting circulation of the blood increasingly and thereby enhancing health.

The reference numeral 30 represents an optical conductor cable. A light focusing device for focusing solar rays or aritifical light rays (such as xenon lamp light rays) is connected to the end portion of the optical conductor cable 30 which not shown in FIG. 1. The light rays focused by the light focusing device is guided into the optical conductor cable 30 and transmitted therethrough. The transmitted light rays consists of only the visible light rays component not containing therein ultraviolet, infrared or the like. The technology of guiding only visible light rays not containing therein ultraviolet, infrared of the like into the optical conductor has been already proposed by the present inventor. Details thereof are omitted here, because of having no direct connection with the present invention.

The reference numeral 22 represents a light-receiving side socket of the optical conductor 20. When the light rays bathtub is employed, the socket 22 is connected with a light-emitting side socket 31 of the optical conductor cable 30. The light rays transmitted through the optical conductor cable 30 as mentioned before are further transmitted through the sockets 22 and 31 into the optical conductor 20. The transmitted light rays are radiated into the light rays bathtub 10 as mentioned before, and the radiated light rays are reflected on the inner wall surface 11 of the light rays bathtub 10, and thereafter applied almost uniformly to the entire skin surface of the person bathing in the reflected light rays.

The temperature in the light rays bathtub 10 is controlled at a desired value. The temperature control is performed, for instance, by supplying thereto air controlled at a desired value for hot or cool temperature through an air-hose 40. When the light rays bathtub is employed, the end portion of the air-hose 40 is connected with an air-hose receiving junction 41 mounted on the upper portion of the light rays bathtub 10, and the temperature-controlled air is supplied to the light rays bathtub 10 from the upper portion thereof and discharged outside from the lower portion thereof.

Furthermore, although only a light rays bathtub for bathing in a state of standing has been described heretofore, it will be possible to bathe while sitting on a chair or lying on a bed. On that occasion, the form of the light rays bathtub is changed corresponding to the state of employment. For instance, the height thereof needs to be lowered a little more or changed for a horizontal type. Such modification of its form can be performed optionally depending on the necessity thereof. On that occasion, if the chair, the bed or the like to be put in the light rays bathtub is constructed with transparent material, the entire body can bathe much more effectively in the light rays bathtub.

As is apparent from the foregoing description, according to the present invention, it is possible to provide a light rays bathtub in which the entire body can bathe effectively in the light rays consisting of only the visible light ray component not containing therein harmful ultraviolet, infrared or the like.

Figure 2:
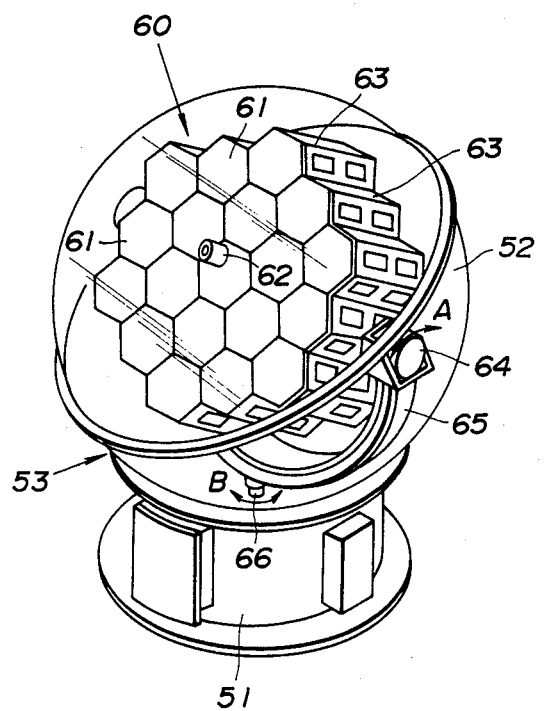
FIG. 2 is a structural view for explaining an embodiment of a solar ray collecting device which is employed for bringing the present invention into operation.

FIG. 2 is a detailed structural view for explaining a solar ray collecting device which is employed for bringing the present invention into operation.

In FIG. 2, 51 is a cylindrical foundation, and 52 is a transparent dome-shaped head portion. The capsule 53 of the solar ray collecting device comprises the foundation 51 and the head portion 52. When the device is used, a solar ray collecting portion 60 is accommodated in the capsule 53 as shown in FIG. 2.

The solar ray collecting device 60 comprises a large number of lenses 61 (nineteen lenses in the embodiment shown in FIG. 2), a solar rays direction sensor 62 for detecting the direction of the solar rays, a support frame 63 for unitarily sustaining the lenses 61 and the solar rays direction sensor 62, a first motor 64 for rotatably moving in a direction shown by an arrow A the unitarily combined lenses 61, sensor 62, and support frame 63, a support arm 65 for supporting the afore-mentioned lenses 61, sensor 62, support frame 63, and motor 64, a rotatable shaft 66 installed so as to meet at a right angle with the rotatable shaft of the afore-mentioned motor 64, and a second motor not shown in FIG. 2 for rotating the rotatable shaft 66 in a direction shown by an arrow B.

The direction of the solar rays is detected by the solar rays direction sensor 62. The signal generated by the sensor 62 controls the first motor and the second motor so as to direct the lenses 61 toward the sun at all times. The solar rays focused by the lenses 61 are guided into the optical conductor cables 30 and 40 shown in FIG. 1, the light receiving end portion of which is located at the focus position of the lenses 61.

I claim:

1. A light ray bathtub comprising a tub means, said tub means comprising a tub member having an opening through which a person can enter and exit the tub member and a cover for covering said opening, said tub means having an inner surface formed as a reflective surface, connector means on said tub means connectable to a source of visible light rays in which said source excludes ultra violet and infrared light ray components, and a plurality of optical conductor means connected to said connector means for receiving said visible light rays and disposed on the inner walls of said tub means for radiating therefrom said visible light rays, said radiated visible light rays being radiated into the interior of said tube means and being reflected from said reflective surface into the interior of said tub means to be thereby applied onto the body of a person inside of said tub means.

2. A light ray bathtub according to claim 1, wherein said optical conductor means comprises a plurality of optical conductors spaced uniformly throughout the inner surface of said tub means to thereby provide uniform radiation of light rays onto the person in said tub means.

3. A light ray bathtub according to claim 1, wherein said optical conductor means comprises a plurality of optical conductors spaced such that there is a greater concentration of optical conductors in one area than in another area such that the visible light rays are radiated with a greater concentration in said one area than in said other area.

4. A light ray bathtub according to claim 1, wherein said cover is made of a transparent material.

5. A light ray bathtub according to claim 1, whrein said tub means is elongate with its longitudinal axis vertically disposed, said cover defining the top end portion of the tub means such that when a person is within the tub means, the person's head is within the cover, said cover being made of a transparent material.

6. A light ray bathtub according to claim 5 further comprising a transparent bottom plate in said tub means disposed generally perpendicular to said vertical axis.

7. A light ray bathtub according to claim 1, wherein said optical conductor means is disposed on the inside surface of said tub member and on the inside surface of said cover.

8. A light ray bathtub according to claim 1 further comprising inlet means on said tub means for supplying air to the interior of said tub means.

9. A light ray bathtub according to claim 1 further comprising an undressing basket mounted on the outside of said tub member.

10. A light ray bathtub according to claim 1 further comprising second connector means on said tub means connectable to a source of artificial light.

11. A light ray bathtub comprising a tub means, said tub means having an inner surface formed as a reflective surface, connector means on said tub means connectable to a source of visible light rays, and a plurality of optical conductor emeans connected to said connector means for receiving said visible light rays and disposed on the inner walls of said tub means for radiating therefrom said visible light rays, said radiated visible light rays being radiated into the interior of said tub means and being reflected from said reflective surface into the interior of said tub means to be thereby applied onto the body of a person inside of said tub means.

* * * * *